(12) United States Patent
Bacus et al.

(10) Patent No.: US 7,031,507 B2
(45) Date of Patent: Apr. 18, 2006

(54) METHOD AND APPARATUS FOR PROCESSING AN IMAGE OF A TISSUE SAMPLE MICROARRAY

(75) Inventors: James W. Bacus, Oakbrook, IL (US); James V. Bacus, Downers Grove, IL (US)

(73) Assignee: Bacus Laboratories, Inc., Lombard, IL (US)

( * ) Notice: Subject to any disclaimer, the term of this patent is extended or adjusted under 35 U.S.C. 154(b) by 0 days.

(21) Appl. No.: 10/271,185

(22) Filed: Oct. 15, 2002

(65) Prior Publication Data

US 2003/0039384 A1 Feb. 27, 2003

Related U.S. Application Data

(63) Continuation of application No. 09/740,711, filed on Dec. 19, 2000, now Pat. No. 6,466,690.

(51) Int. Cl.
G06K 9/00 (2006.01)
(52) U.S. Cl. ....................... 382/133; 382/318
(58) Field of Classification Search ............... 382/128, 382/133, 134, 284, 294, 305, 306, 318; 128/922; 356/39; 702/21; 348/79; 345/634, 635; 707/100, 102, 104.1
See application file for complete search history.

(56) References Cited

U.S. PATENT DOCUMENTS

| | | | |
|---|---|---|---|
| 3,999,047 A | 12/1976 | Green | 235/151.3 |
| 4,150,360 A | 4/1979 | Kopp et al. | 340/146.3 P |
| 4,175,860 A | 11/1979 | Bacus | 356/39 |
| 4,199,748 A | 4/1980 | Bacus | 340/146.3 CA |
| 4,213,036 A | 7/1980 | Kopp et al. | 235/92 PC |
| 4,523,278 A | 6/1985 | Reinhardt et al. | 364/413 |
| 4,741,043 A | 4/1988 | Bacus | 382/6 |
| 4,742,558 A | 5/1988 | Ishibashi et al. | 382/56 |
| 4,760,385 A | 7/1988 | Jansson et al. | 340/709 |
| 4,777,525 A | 10/1988 | Preston, Jr. | 358/102 |
| 4,820,504 A | 4/1989 | Battifora | 424/3 |
| 4,887,892 A | 12/1989 | Bacus | 350/523 |
| 4,914,022 A | 4/1990 | Furmanski et al. | 435/7 |
| 4,965,725 A | 10/1990 | Rutenberg | 364/413.1 |
| 5,018,209 A | 5/1991 | Bacus | 382/6 |
| 5,068,906 A | 11/1991 | Kosaka | 382/48 |
| 5,072,832 A | 12/1991 | Valentine et al. | 206/570 |
| 5,073,857 A | 12/1991 | Peters et al. | 364/413.1 |
| 5,099,521 A | 3/1992 | Kosaka | 382/6 |

(Continued)

FOREIGN PATENT DOCUMENTS

EP 0 209 422 A1 1/1987

(Continued)

OTHER PUBLICATIONS

U.S. Appl. No. 09/971,742, filed Sep. 19, 2002, Kallioniemi et al.

(Continued)

*Primary Examiner*—Andrew W. Johns
(74) *Attorney, Agent, or Firm*—Fitch, Even, Tabin & Flannery

(57) ABSTRACT

A method and apparatus for processing an image of a tissue sample microarray include placing a plurality of tissue samples in an array on a microscope slide. The tissue samples are then simultaneously and uniformly treated, as by staining. Images of the tissue making up the microarray are captured and stored together with identifying information related thereto. The images may be displayed from the digital storage medium using a programmed processor which can select various magnifications for display. The images also can be accessed by network and remotely.

53 Claims, 9 Drawing Sheets

U.S. PATENT DOCUMENTS

| | | | | |
|---|---|---|---|---|
| 5,107,422 | A | 4/1992 | Kamentsky et al. ... | 364/413.08 |
| 5,123,056 | A | 6/1992 | Wilson ............................ | 382/6 |
| 5,163,095 | A | 11/1992 | Kosaka ............................ | 382/6 |
| 5,216,500 | A | 6/1993 | Krummey et al. .............. | 358/93 |
| 5,216,596 | A | 6/1993 | Weinstein ............... | 364/413.02 |
| 5,218,645 | A | 6/1993 | Bacus ............................. | 382/6 |
| 5,252,487 | A | 10/1993 | Bacus et al. ................... | 436/63 |
| 5,257,182 | A | 10/1993 | Luck et al. .............. | 364/413.1 |
| 5,260,871 | A | 11/1993 | Goldberg ............... | 364/413.02 |
| 5,268,966 | A | 12/1993 | Kasdan ........................... | 382/6 |
| 5,287,272 | A | 2/1994 | Rutenberg et al. ...... | 364/413.01 |
| 5,297,034 | A | 3/1994 | Weinstein ............... | 364/413.02 |
| 5,313,532 | A | 5/1994 | Harvey et al. ................. | 382/15 |
| 5,333,207 | A | 7/1994 | Rutenberg ...................... | 382/6 |
| 5,428,690 | A | 6/1995 | Bacus et al. ................. | 382/133 |
| 5,473,706 | A | 12/1995 | Bacus et al. ................. | 382/133 |
| 5,499,097 | A | 3/1996 | Ortyn et al. ................. | 356/372 |
| 5,505,946 | A | 4/1996 | Kennedy et al. .......... | 424/195.1 |
| 5,544,650 | A | 8/1996 | Boon et al. ................... | 128/632 |
| 5,625,765 | A | 4/1997 | Ellenby et al. .............. | 395/135 |
| 5,655,029 | A | 8/1997 | Rutenberg et al. ........... | 382/133 |
| 5,687,251 | A | 11/1997 | Erler et al. .................. | 382/133 |
| 5,784,162 | A | 7/1998 | Cabib et al. ................. | 356/346 |
| 5,793,969 | A | 8/1998 | Kamentsky et al. ... | 395/200.43 |
| 5,796,861 | A | 8/1998 | Vogt et al. ................... | 382/128 |
| 5,836,877 | A | 11/1998 | Zavislan ...................... | 600/407 |
| 5,838,837 | A | 11/1998 | Hirosawa et al. ........... | 382/284 |
| 5,863,877 | A | 1/1999 | Carr et al. ................... | 510/348 |
| 5,978,804 | A | 11/1999 | Dietzman .................... | 707/10 |
| 5,993,001 | A | 11/1999 | Bursell et al. ............... | 351/212 |
| 6,031,930 | A | 2/2000 | Bacus et al. ................. | 382/133 |
| 6,044,755 | A | 4/2000 | Misceo ......................... | 99/332 |
| 6,078,681 | A | 6/2000 | Silver .......................... | 382/133 |
| 6,091,842 | A | 7/2000 | Domanik et al. ............ | 382/133 |
| 6,091,930 | A | 7/2000 | Mortimer et al. ........... | 434/362 |
| 6,101,265 | A | 8/2000 | Bacus et al. ................. | 382/133 |
| 6,137,897 | A | 10/2000 | Emi et al. .................... | 382/128 |
| 6,148,096 | A | 11/2000 | Pressman et al. ........... | 382/133 |
| 6,151,405 | A | 11/2000 | Douglass et al. ............ | 382/133 |
| 6,362,004 | B1 | 3/2002 | Noblett ........................ | 436/43 |
| 6,362,832 | B1 | 3/2002 | Stephan et al. ............. | 345/629 |
| 2002/0025082 | A1* | 2/2002 | Kaushikkar et al. ........ | 382/294 |
| 2002/0106119 | A1* | 8/2002 | Foran et al. ................. | 382/133 |
| 2003/0118222 | A1* | 6/2003 | Foran et al. ................. | 382/128 |
| 2003/0133009 | A1* | 7/2003 | Brown et al. ................. | 348/61 |
| 2003/0138827 | A1 | 7/2003 | Kononen et al. .............. | 435/6 |

FOREIGN PATENT DOCUMENTS

| | | |
|---|---|---|
| EP | 0 246 010 A1 | 11/1987 |
| JP | 05-313071 A | 11/1993 |
| JP | 06-118307 A | 4/1994 |
| JP | 07-015721 A | 1/2005 |
| WO | WO 98/39728 A1 | 9/1998 |
| WO | WO 98/44446 A1 | 10/1998 |
| WO | WO 99/44062 A1 | 9/1999 |
| WO | WO 99/44063 A2 | 9/1999 |
| WO | WO 01/42796 A1 * | 6/2001 |

OTHER PUBLICATIONS

U.S. Appl. No. 10/215,762, filed Dec. 19, 2002, Kononen et al.

U.S. Appl. No. 60/075,979, filed Sep. 2, 1999, Kononen et al.

U.S. Appl. No. 60/106,038, filed Sep. 2, 1999, Kallioniemi et al.

U.S. Appl. No. 60/150,493, filed Sep. 19, 2002, Kallioniemi et al.

Szeliski R: "*Image Mosaicing For Tele-Reality Applications*" Proceedings of the IEEE Workshop on Applications of Computer Vision, XX, XX, May 1, 1994, pp. 44-53, XP 002048809.

Krishnan A et al.: "*Panoramic Image Acquisition*" Proceedings 1996 IEEE Computer Society Conference on Computer Vision and Pattern Recognition (CAT No. 96CB35909), Proceedings of IEEE Conference on Computer Vision and Pattern Recognition, San Francisco, CA, USA Jun. 18-20, 1996.

Szeliski et al.; "*Direct Methods for Visual Scene Reconstruction*" Digital Equipment Corporation Cambridge Research Lab, pp. 26-33, Jun. 24, 1995.

Dani et al.: "*Automated Assembling of Images: Image Montage Preparation*" Department of Electrical Engineering, Indian Institute of Technology, pp. 431-445, Oct. 24, 1993.

Charles W. Boone and Gary J. Kelloff, "*Biomarkers of Premalignant Breast Disease and Their Use as Surrogate Endpoints in Clinical Trials of Chemopreventive Agents*" The Breast Journal vol. 1, No. 4, pp. 228-235 (1995), 8 pages.

Norman J. Pressman, "*Markovian Analysis of Cervical Cell Images*" The Journal of Histochemistry and Cytochemistry vol. 24, No. 1, pp. 138-144 (1976), 7 pages.

"*The CAS 200™ Multiscan™ Automated Pathology Workstation*" by James V. Bacus, Compendium on the Computerized Cytology and Histology Laboratory, Tutorials of Cytology ©1994.

Barlund, M. et al., "*Detecting Activation of Ribosomal Protein S6 Kinase by Complementary DNA and Tissue Microarray Analysis*." J. Natl Cancer Inst, 2000. 92(15): p. 1252-9.

Barlund, M. et al., "*Multiple Genes at 17Q23 Undergo Amplification and Overexpression in Breast Cancer*." Cancer Res, 2000. 60(19): p. 5340-4.

Bowen, C. et al., "*Loss of NKX3.1 Expression in Human Prostate Cancers Correlates With Tumor Progression*." Cancer Res, 2000. 60(21): p. 6111-5.

Bucher, C. et al., "*Automated High-Throughput Tissue Array Analysis for Assessing the Significance of HER-2 Involvement in Breast Cancer*." ASCO Abstract 2388, 2000.

Bubendorf, L. et al., "*Survey of Gene Amplifications During Prostate Cancer Progression of High-Throughout Fluorescence in Situ Hybridization on Tissue Microarrays*." Cancer Res, 1999. 59(4): p. 803-6.

Bubendorf, L. et al., "*Hormone Therapy Failure in Human Prostate Cancer: Analysis by Complementary DNA and Tissue Microarrays*." J Natl Cancer Inst. 1999. 91(20): p. 1758-64.

Camp, R.L., L.A. Charette, and D.L. Rimm, "*Validation of Tissue Microarray Technology in Breast Carcinoma*." Lab Invest, 2000.80(12): p. 1943-9.

Ingvarsson, S. et al., "*Reduced FHIT Expression in Sporadic and BRCA2-Linked Breast Carcinomas*." Cancer Res, 1999. 59(11): p. 2682-9.

Kononen, J. et al.; "*Tissue Microarrays for High-Throughput Molecular Profiling of Tumor Specimens*." Nat Med, 4:844-847,1998.

Kononen, J., "*Introduction to Tissue Array Technology*," presented at the National Cancer Institute Working Group meeting on Tissue Microarrays, Dec. 16-17, 1999.

Lee, S.K. et al., "*A Nuclear Factor, ASC-2, as a Cancer-Amplified Transcriptional Coactivator Essential for Ligand-Dependent Transactivation by Nuclear Receptors in Vivo.*" J Biol Chem, 1999. 274(48): p. 34283-93.

Moch, H. et al., "*High-Throughput Tissue Microarray Analysis to Evaluate Genes Uncovered by cDNA Microarray Screening in Renal Cell Carcinoma.*" Am J Pathol, 1999. 154(4): p. 981-6.

Perrone. E.E. et al., "*Tissue Microarray Assessment of Prostate Cancer Tumor Proliferation in African-American and White Men.*" J Natl Cancer Inst, 2000.92(11): p. 937-9.

Richter, J. et al., "*High-Throughput Tissue Microarray Analysis of Cyclin E Gene Amplification and Overexpression in Urinary Bladder Cancer.*" Am J Pathol, 2000. 157(3): p. 787-94.

Sallinen, S.L. et al., "*Identification of Differentially Expressed Genes in Human Gliomas by DNA Microarray and Tissue Chip Techniques.*" Cancer Res, 2000. 60(23): p. 6617-22.

Schraml, P. et al., "*Tissue Microarrays for Gene Amplification Surveys in Many Different Tumor Types.*" Clin Cancer Res, 1999. 5(8): p. 1966-75.

Shah, R., "*Postatrophic Hyperplasia of the Prostate Gland: Neoplastic Precursor or Innocent Bystander?*" Am J Pathol, 2001. 158(5): 1767-1773 (Presented at 2000 USCAP (Mar, New Orleans, LA) & the American Urological Associates (May 2000, Atlanta, GA).

Shibata, D. "*Pattern Recognition and Arrays, The Time are A-Changing.*" Am J Pathol, 1999. 154(4): p. 979-80.

* cited by examiner

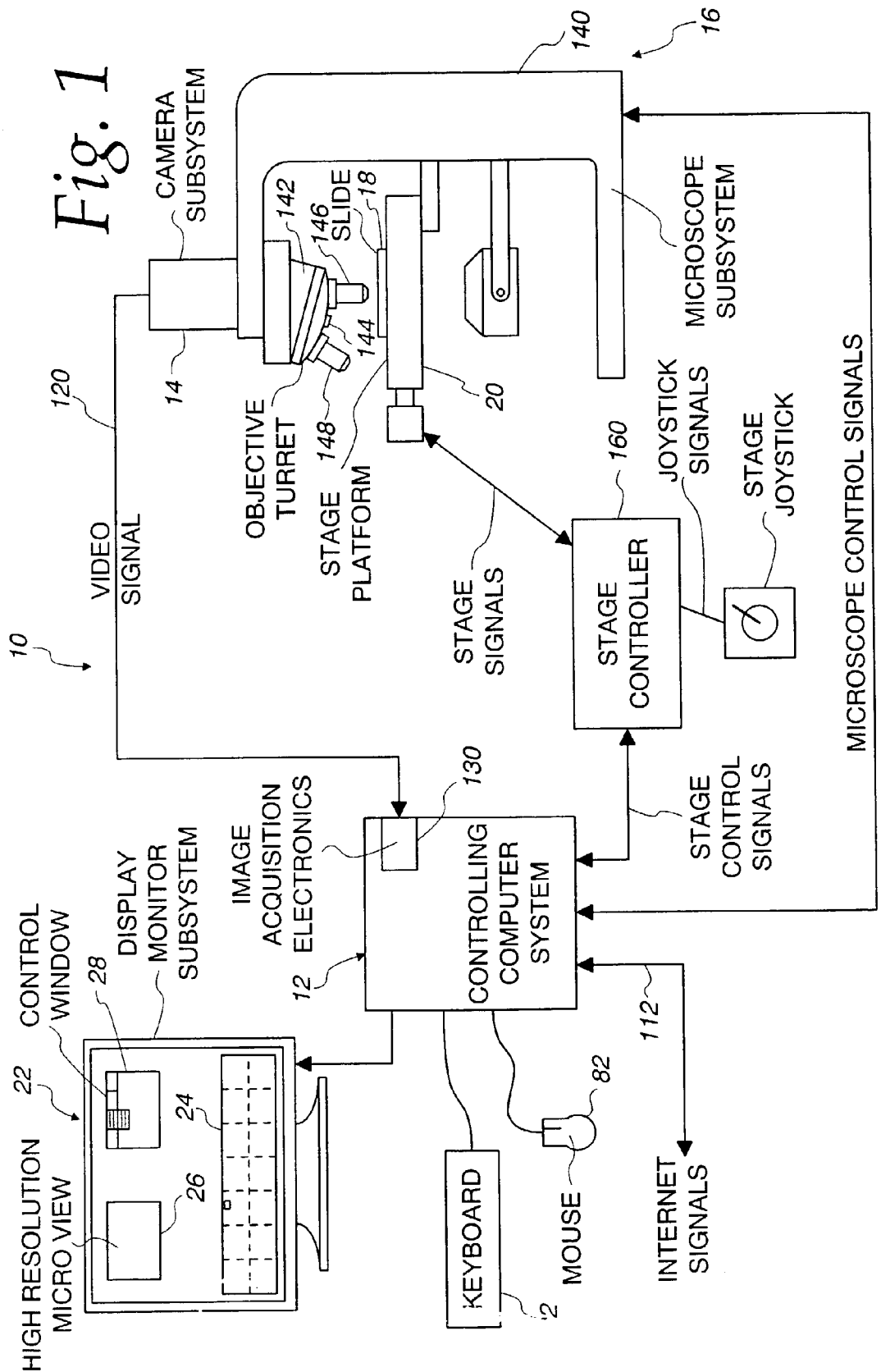

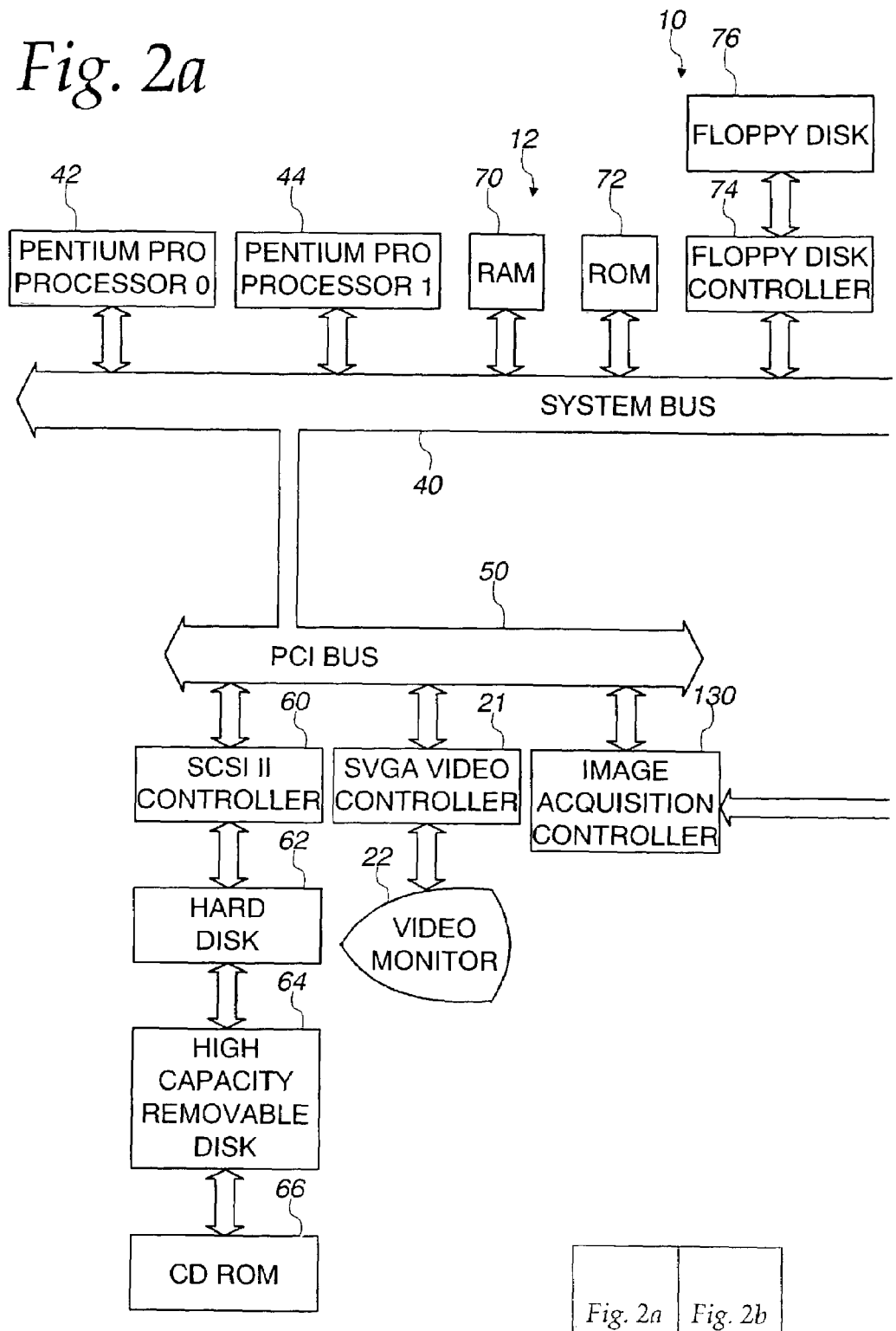

METHOD AND APPARATUS FOR PROCESSING AN IMAGE OF A TISSUE SAMPLE MICROARRAY

FIELD OF THE INVENTION

This is a continuation of prior application Ser. No. 09/740,711, filed Dec. 19, 2000, U.S. Pat. No. 6,466,690 which is hereby incorporated herein by reference in its entirety

BACKGROUND OF THE INVENTION

The invention relates in general to a method and apparatus for processing images of a tissue sample microarray made up of a plurality of tissue microarray dots using an optical microscope. More particularly, the invention relates to a method and apparatus for capturing tissue sample images from the tissue sample microarray, indexing such images and manipulating and transmitting them.

It is known that in the treatment and prevention of cancers it is often important periodically to examine persons at risk for cancer. In some instances it may be necessary to biopsy tissue from such persons. As medical care has become available to more people and as the need for such increased vigilance has been recognized, the number of biopsies has increased.

One of the problems with evaluating biopsy materials is that in most cases microscopic evaluation of cellular structure and tissue architecture has been important in making determinations as to whether cellular changes have occurred in tissues indicative of cancer or whether cancer is actually present. In the past, such determinations have been made by employing microscopic examinations of tissues and associated cellular structures.

A number of techniques have been developed, including techniques developed by the present inventors, for providing greater accuracy and throughput for such biopsy systems.

In one such system tissues from a particular patient which have been stained are positioned from a particular patient on a microscope slide and are imaged by a light microscope. The images are captured and digitized in a tiled format. The tiles can be reassembled substantially in real time to create pan and scan images of large amounts of tissue at high magnification while simultaneously providing a second digitized image of tissue at low magnification to provide a guide to regions of interest of the pathologist. This system has proven to be a boon to pathologists.

Improvements made upon that system, such as that disclosed in U.S. Pat. No. 6,031,930 to Bacus et al., are directed to further enhancements of the microscopic image examination in that detailed features of the morphometry of images of microscopic objects, such as cells, cell fragments, and the like, are made more easy. Statistical measures are applied which are highly discriminating for neoplasia across diverse tissue types, such as breast, colon, cancer, cervical tissue, and the like. In addition, such systems are valuable in providing assaying functions for different carcinogens and chemopreventive agents.

More specifically, such systems use microscopic images of stained neoplastic tissue sections which are microscopically scanned to provide electronic or digitally recorded. Morphometric features of tissue sample images are measured in first unit values and texture measurements of the tissue samples, such as a Markovian texture measurement, are also made. The respective results are recorded on a grading common scale so that progression of cancer can be ascertained relative to normal tissue.

An additional advance has been made, as exemplified by U.S. Pat. No. 6,101,265 to Bacus et al. Bacus et al. disclose the use of an imaging system which can scan stained tissue samples on microscope slides and generate tiled images thereof. The system also provides low and high magnification image pan and scan capability both locally and remotely. Typical magnifications are 1.25 power, 4 power, 20 power, and 40 power. This allows a pathologist at a remote site to be able to examine a complete and accurate magnified record of the tissue. This can occur over a packet network, such as the Internet or the like, without the need for a wide-band, high-speed transmission, such as a television line.

Despite each of the advantages which have been provided by the previous systems, they still have some drawbacks when presented with newer technologies for rapid assay of large amounts of tissue. Recently, molecular profiling of tissue specimens has come into wider use. This process has to do with the discovery of new genes and targeting genetic probes for attachment to particular tissue regions and molecules such as epitopes. Pharmaceutical companies and researchers in the biological sciences are interested in developing antibody-based probes using standard antibody staining reactions in order to detect molecular abnormalities on the surfaces of cells.

In order to assay such wide collections of patients, it is necessary to collect large amounts of data from the patients. It is known to prepare tissue sample microarrays which consist of a plurality of circular sections of tissue drawn from a variety of persons or sampling sites and placed on a single microscope slide. Such samples are prepared by taking a very small diameter punch, removing punch cores of tissue and placing them into open columns in a paraffin block which open columns are arranged in a grid type array which may for instance have two to three hundred columns available. The total size of the block is small enough that an end section of the block would conveniently fit on a microscope slide under a cover glass or cover slip. Once the columns of tissue are placed within the block, the block is further treated so that the paraffin invades the tissue to provide a typical paraffin biological specimen. The block may be sectioned using separate microtome sectioning techniques and the sections with the two to three hundred circular tissue sample "dots" may be placed on a microscope slide.

The slide may be subjected to staining and other antibody treatment and has the particular advantage that all two to three hundred of the specimens in the microarray are subjected to simultaneous and identical staining conditions, temperature conditions, and the like, so that variables need not be controlled for between patients who are being examined and a standardized treatment as applied to the tissue.

One of the problems, however, with such microarray-based assays is that the slides must be processed by hand. A microscopic determination must be made of characteristics of each of the tissue samples. At times tissue dots may fall off the slides opening up voids in the array or grid. It is easy for researchers who are examining the slides to lose track of which piece of tissue is being examined.

Although the microarray staining techniques have provided a considerable advantage in speeding up molecular assaying, the analysis of such results continues to be time-consuming and may be subject to more increased error than other types of assay systems.

What is needed then is a system which would provide for rapid assay of a microarray by an operator so that the advantages of bulk microarray treatment techniques can be fully realized.

SUMMARY OF THE INVENTION

A method and apparatus for processing an image of a tissue sample microarray include placing a plurality of tissue samples in an array or a rectangular grid on a conventional glass microscope slide. The tissue samples, which have been sectioned and form the array, may then be treated simultaneously as by staining the entire slide with a suitable biological stain for providing contrast to image various structures within the tissues or cells making up the multiple samples of the microarray. The advantage of doing this is that it allows multiple samples taking from multiple patients to be treated in substantially the same way and reduces the number of controls which must be put in place during the experiment.

The tissue sample microarray is prepared by taking a core or "punch" of tissue from a tissue sample the core may have a diameter of a millimeter or less and the cored tissue is inserted into an open channel which is a right circular cylinder channel which is one of a rectangular array of channels formed in a paraffin block. The paraffin block is then treated so that the paraffin enters the tissue which is placed into each of the channels. The block may then be sectioned by a microtome as are other paraffin block tissue samples. The microtome section may then be lifted and then placed on a microscope slide in a conventional manner. In this manner one or more microarrays may be placed on a single microscope slide. The microarrays typically have two to three hundred dots of tissue thereon, there may be up to six microarrays on a slide for over one thousand tissue samples on the slide which are subjected to substantially the same staining treatment. After staining, washing and the like are completed a cover slip is placed on the slide to make the slide permanent.

The slide may be placed on a movable stage of a scanning microscope. The microscope allows the user to take a low magnification image of a plurality of tissue dots in the microarray grid. The user may then identify corners of a scanned pattern. The scan pattern is usually rectangular and encompasses a subset of the tissue dots which are to be scanned.

An imager, optically connected to receive images from the microscope, generates a digital image which is fed to a processor and displayed on a display. The displayed image identifies the four corners of the grid to be scanned. It then shows target points at what would be expected to be the center points of the tissue dots in the grid array. Sometimes the dots are not precisely registered with uniform center-to-center distances within the array. Some tissue dots even may be missing. The user is then prompted with a cross-hair in each of the dots. Through the use of a mouse-select and drag operation the user can re-center the dot center point for the scan within each dot.

Once this has been done tiling grids are constructed and displayed over each of the images of the selected tissue dots. The tiling grids may typically include three rows and three columns of rectangular image tiles per tissue dot image. Tiling does not take place in the substantially empty or dot-free portions of the microarray.

The user may then command the computer to tile at least a portion of the dot images in the microarray. This consists of the microscope stage receiving commands at its X and Y stepper motors and then moving its stage and the slide it carries to a first position in a particular tile grid array of a selected dot image. A first dot image tile is captured. The stage is moved to the next tile position for that tissue dot and the next tile image is captured. In this manner all of the high magnification tile images at 20 to 40 power for that particular dot are captured. After completion of the capture of the first set of tile images for that dot additional capture takes place at successive tissue dots until the tiled images of all tissue dots within the selected tissue dot sub-array are captured.

After the dot images are captured data structures are set up associating block identification, user identification and patient identification with each of the tiled dot images. The specific identifying information at the block, user and patient levels may be inserted by the operator of the microscope at the time of dot image capture or later. In this way the tiled tissue dot microarray images are directly associated with the tissue dots in storage so that even if the original tissue microarray slide is lost the visual information and identifying information associated with the project would not be lost.

It is a principal aspect of the present invention to provide an image processing system which rapidly and completely scans and captures low magnification and high magnification images of a microarray of tissue specimens.

It is another aspect of the present invention to provide a method and apparatus for associating each of the images of the tissue samples or tissue dots within the microarray with a unique identifier so that the dot images can later be identified and accessed and be quickly and easily evaluated.

Other aspects and advantages of the present invention will become obvious to one of ordinary skill in the art upon appraisal of the remainder of the specification in light of the accompanying drawings and claims.

BRIEF DESCRIPTION OF THE DRAWINGS

FIG. 1 is a block diagram of an apparatus embodying the present invention;

FIGS. 2A and 2B are block diagrams of a portion of the apparatus shown in FIG. 1;

DETAILED DESCRIPTION OF THE PREFERRED EMBODIMENT

Figure 2B:
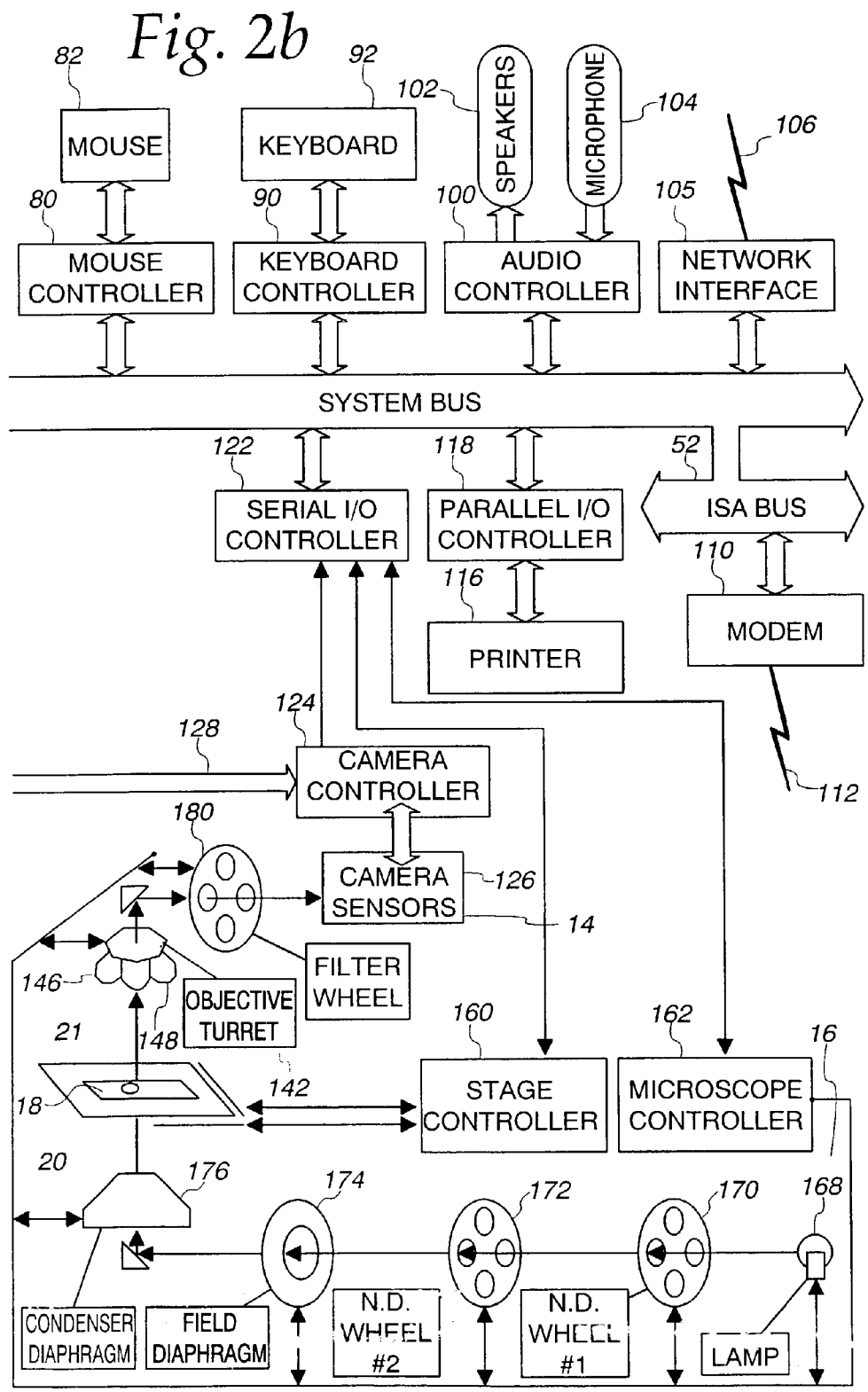
Figure 3:
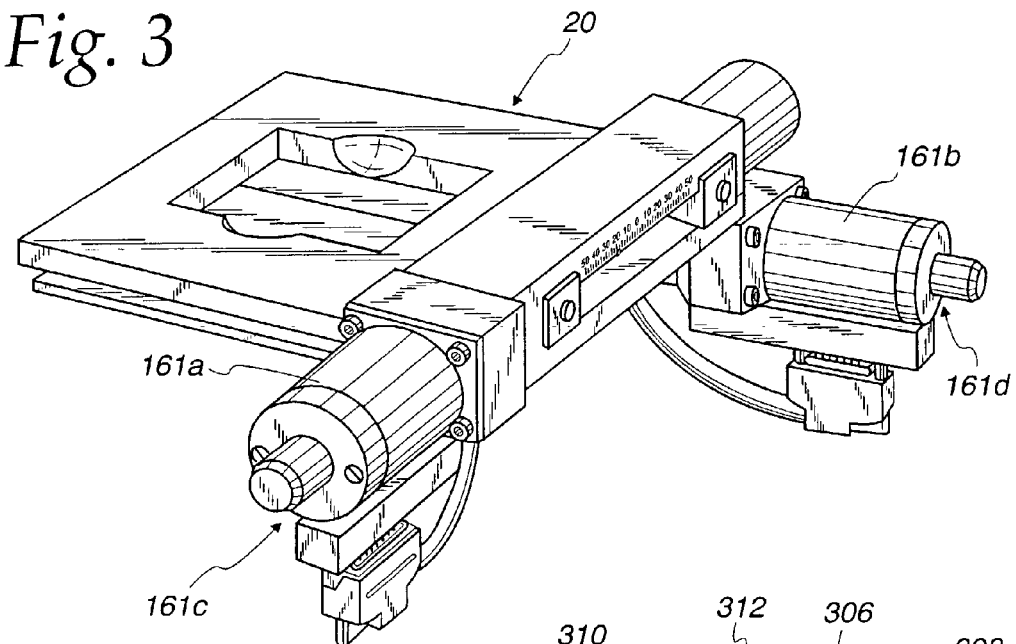
FIG. 3 is a perspective view of a microscope stage assembly including stepper motors for moving a slide-holding stage, and shaft encoders for indicating stage position and providing a closed loop drive for the stepper motors.

Referring now to the drawings and especially to FIG. 1, an apparatus embodying the present invention is shown therein and generally identified by reference numeral 10. The apparatus 10 is adapted for synthesizing low magnification and high magnification microscopic images of tissue sample microarrays. The apparatus 10 includes a computer 12 which is a dual microprocessor personal computer in combination with a Hitachi HV-C20 video camera 14 associated with a Zeiss Axioplan 2 microscope 16. The computer system 12 receives signals from the camera 14 which captures light from the microscope 16 having a microscope slide 18 positioned on an LUDL encoded motorized stage 20. The encoded motorized stage 20 includes a MAC 2000 stage controller for controlling the stage in response to the computer 12.

A microscope slide 18 includes a plurality of tissue sample microarrays 19 each comprising a tissue sample microarray made up of a grid or array of circular tissue sample sections or dots 21, which are to be viewed by the microscope and whose images are to be digitized both at low magnification and at high magnification as selected by a user. The low magnification digitized image is then displayed on a 21 inch Iiyama video display monitor 22 having resolution of 1600 by 1200 to provide display screens of the type shown in FIG. 1 including a high magnification image 26, for instance at 40 power and a control window or image 28. A low magnification image may also be generated separately or simultaneously on the screen so that a pathologist or other operator of the system can review architectural regions of interest in low magnification and simultaneously view them in high magnification in the high magnification screen or window 26 to determine whether the cells forming a portion of the architectural feature need be examined further for cancer or the like or not.

The computer 10 is constructed around a PCI system bus 40 although other bus structures such ATX may be used. A first microprocessor 42 and a second microprocessor 44 are connected thereto. The microprocessors may be Pentium III or the like high performance microprocessors. The system bus 40 has connected to it a PCI bus 50 and an ISA bus 52. The PCI bus 50 has a SCSI controller 60 connected thereto to send and receive information from a hard disk 62. The hard disk 62 also is coupled in daisy-chained SCSI fashion to a high capacity removal disk and to a CD-ROM drive 66. The hard disk 62 contains the programs for operating the system for controlling the microscope 16 and for processing the images as well as for performing a quantitative analysis of the selected portions of the tissue sample microarrays 19 being viewed on the slide 18.

The system bus 40 also has connected to it a random access memory (RAM) 70 within which portions of the program being executed are stored as well as a read only memory (ROM) 72 for holding a bootstrap loader and portions of a basic input/output operating system. A floppy disk controller 74 is coupled to the system bus 40 and has connected to it a floppy disk drive 76 for reading and writing information to a floppy disk as appropriate.

A mouse controller 80 is coupled to the system bus 40 and has a mouse 82 which operates as a pointing device for controlling manipulations on the screen 22 and within the windows 24, 26 and 28. A keyboard controller 90 is connected to the system bus 40 and has a keyboard 92 connected thereto. The keyboard 92 may be used to send and receive alphanumeric signals and control signals to other portions of the computer.

An audio controller 100 has a plurality of speakers 102 and a microphone 104 connected thereto for audio input and output and is coupled to the system bus 40. A network interface, such as a network interface card 104, is connected to the system bus 40 and can provide signals via a channel 106 to other portions of a network or the Internet to which the system may be connected. Likewise, signals can be sent out of the system through a modem 110 connected to the ISA bus 52 and may be sent via a channel 112, for instance, to the Internet. A printer 116 is connected via a parallel I/O controller 118 to the system bus 40 in order to provide printouts, as appropriate, of screens and other information as they are generated. A serial I/O controller 122 is connected to the system bus 40 and has connected to it a camera controller 124 which is coupled to CCD sensors 126 in the cameras. The CCD sensors 126 supply pixel or image signals representative of what is found on the slide 18 to an Epix pixci image acquisition controller 130 coupled to the PCI bus 50.

The microscope 16 includes a base 140 having a stage 20 positioned thereon as well as an objective turret 142 having a plurality of objectives 144, 146 and 148 thereon. The objective 144, for instance, may be of 1.25× objective. The objective 146 may be a 20× objective. The objective 148 may be a 40× objective. Signals from the CCD sensors 126 and controller are supplied over a bus 128 to the image acquisition system where they are digitized and supplied to the PCI bus for storage in RAM or for backing storage on the hard disk 62.

When a tissue sample microarray 19 is on the slide 18 the stage 20 may be manipulated under the control of the computer through a stage controller 160 coupled to the serial I/O controller 122. The stage controller sends motion commands to a pair of stepper motors 161a and 161b. A pair of shaft encoders 161c and 161d send stage position signals back. Likewise, a microscope controller 162 controls operating characteristics of the microscope 16 such as illumination, color temperature or spectral output of a lamp 168 and the like. For instance, in normal operation, when a tissue sample microarray slide 18 is placed on the stage 20, as shown in FIG. 1, the processors 42 or 44 send a command through the system bus to cause the serial I/O controller 122 to signal the microscope controller to change magnification to 1.25× in a step 202. This is done by rotating the objective turret of the Axioplan 2 microscope to select the objective 144. Likewise, the controller sets the color temperature of the lamp 168, sets a pair of neutral density filter wheels 170 and 172 and sets a field diaphragm 174 for the correct illumination. A condenser diaphragm 176 is also controlled. A color filter wheel 180 may also be controlled to apply the appropriate filter color to the CCD sensors 126 in the camera.

In order to provide a magnification called for in, the overall illumination and control of the microscope will be controlled so that the objective turret 142 will be rotated to place the higher power objective above the slide 18. The voltage to the lamp will be changed to adjust the lamp 168 to provide the proper illumination and color temperature as predetermined for the selected objective. The condenser diaphragm 176 will have its opening selected as appropriate to provide the proper illumination for that objective.

The filter turret 180 will select the proper light wavelength filter to be supplied to the camera sensors. For instance, a red, blue, or green filter, as appropriate, particularly if the specimen has been stained. The field diaphragm 174 will have its opening changed. The neutral density filter wheel 170 will select a neutral density filter and the neutral density filter wheel 172 will also select a neutral density filter. The X, Y and Z offsets will be used for reconstruction of the recorded image at the selected magnification. The current stage or slide position will be read from encoders in the stage which are accurate to 0.10 micron.

A substantially rectangular paraffin block 300 comprised of a substantially rectangular section of paraffin 302 has a plurality of columns of tissue 304 embedded therein and extending substantially through the block to form a block microarray. A section 306 is shown as being partially removed from the block as by a microtome (not shown). The section 306 comprises a layer of paraffin 308 having a plurality of tissue dots 310 formed in rows and columns to define a substantially rectangular microarray 312.

Figure 4:
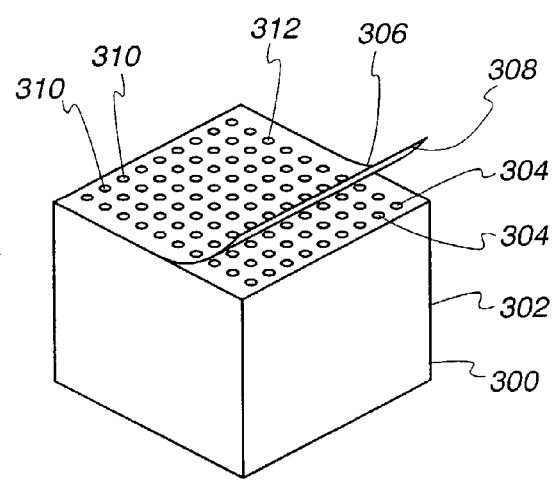
FIG. 4 is a perspective of a microarray slice being separated from a tissue sample paraffin block containing a plurality of plugs of tissue.
Figure 5:
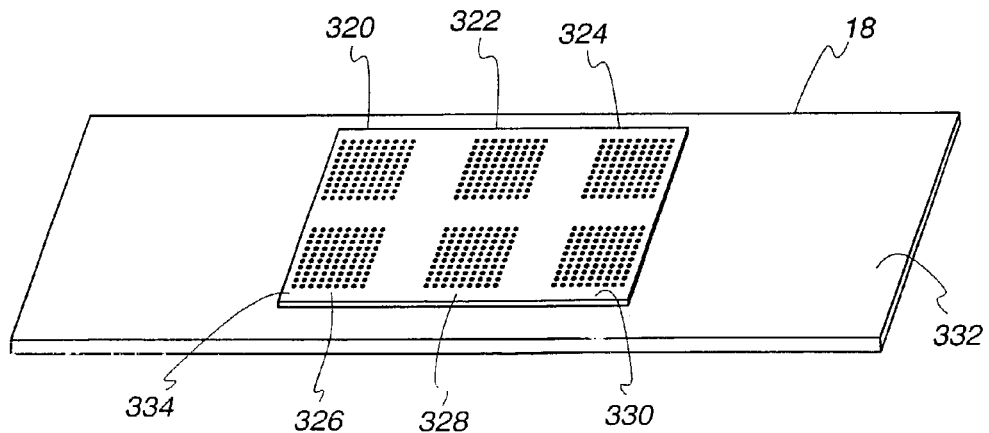
FIG. 5 is a perspective view of a microscope slide carrying multiple microarrays.

It may be appreciated that one or more of these arrays may be placed on the slide 18 as is shown in FIG. 5. A plurality of microarrays, respectively numbered 320, 322, 324, 326, 328 and 330, is placed on a surface 332 of the slide 18 under a conventional cover slip 334. The microarrays are obtained from sections of paraffin blocks of the type shown in FIG. 4 and are placed on the slide 18. The slide 18 is then treated by staining or exposing it to molecular probes. All of the tissue dots in each of the microarrays 320–330 are uniformly treated and exposed to the stain thus controlling for what would otherwise amount to staining differences from slide to slide.

Figure 6:
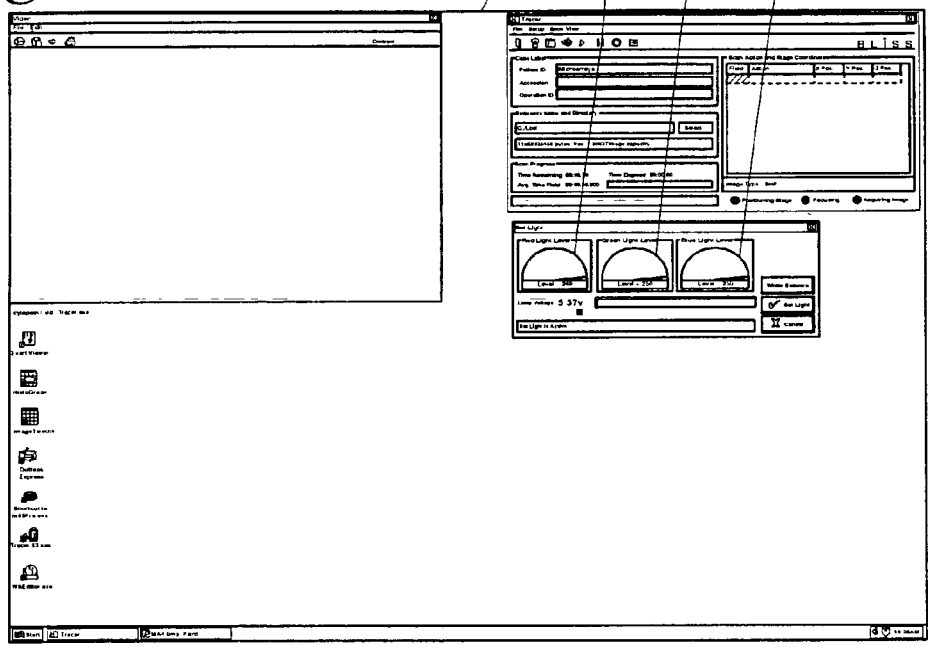
FIG. 6 is a view of a set-up screen for setting the red, green, and blue light levels for a scanning microscope shown in FIG. 1.

The slide 18 is then placed on a stage of the microscope. The microscope has its light level adjusted through the use of a dialog box. As may best be seen in FIG. 6 a dialog box 340 shows a red light level indication 342, a green light level indication 334, and a blue light level indication 346. The light level may be adjusted prior to scanning the microarray.

Figure 7:
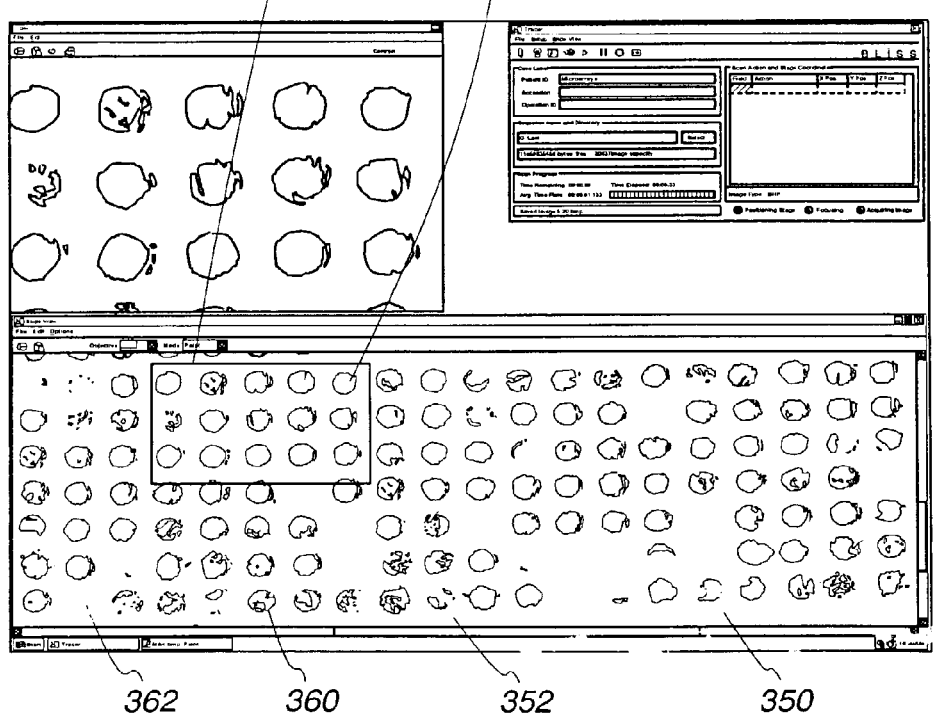
FIG. 7 is a view showing the selection of a subset of the dots in a microarray to be scanned for the apparatus shown in FIG. 1.

The microarray may be initially at low power scanned and a scanned relatively low magnification image 350 stored in the computer memory and displayed in a window 352, as shown in FIG. 7. In order to determine greater detail of a plurality of tissue dots 360 in a microarray 362 a boundary may be defined around the dots as shown by the rectangular boundary 364 by doing a click and drag operation using the mouse. The tissue dots 366 shown within the rectangular region 364 are then selected to be scanned at high magnification.

Figure 8:
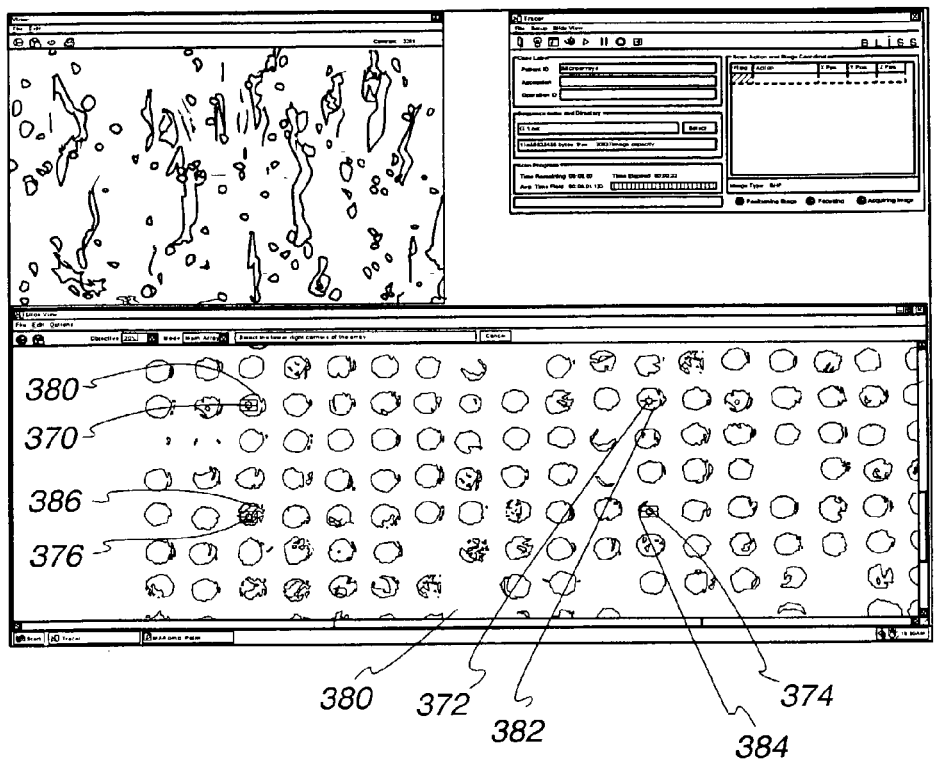
FIG. 8 is a screen shot for a dot scan path configuration for the apparatus shown in FIG. 1.

As may best be seen in FIG. 8 a plurality of corner points 370, 372, 374, and 376 are shown in the low magnification dot array window 330. The corner points are initially positioned near the centers of respective tissue dots 380, 382, 384 and 386. On the basis of the selection of those corner points the system then generates center points for each of the tissue dots assumed to be within the array region.

Figure 9:
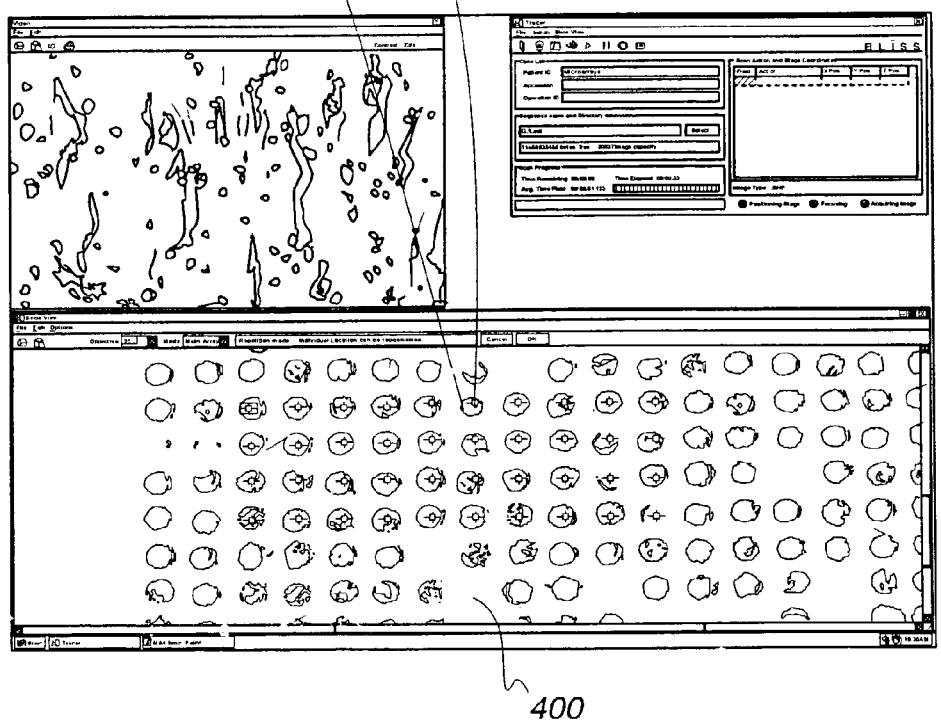
FIG. 9 is a screen shot showing a method of repositioning the areas to be scanned in registration with the actual images of the tissue array dots for the apparatus shown in FIG. 1.

As may best be seen in FIG. 9 and as shown in the window 400, the center points are shown with cross-hairs and blocks as the exemplary center point 402 is shown within a tissue dot 404. Since it may be appreciated that the preselected center points may not be strictly in registration with the tissue dots the operator of the system may click and drag the center point within a dot and recenter it prior to allowing the dot to be scanned at high magnification.

Figure 10:
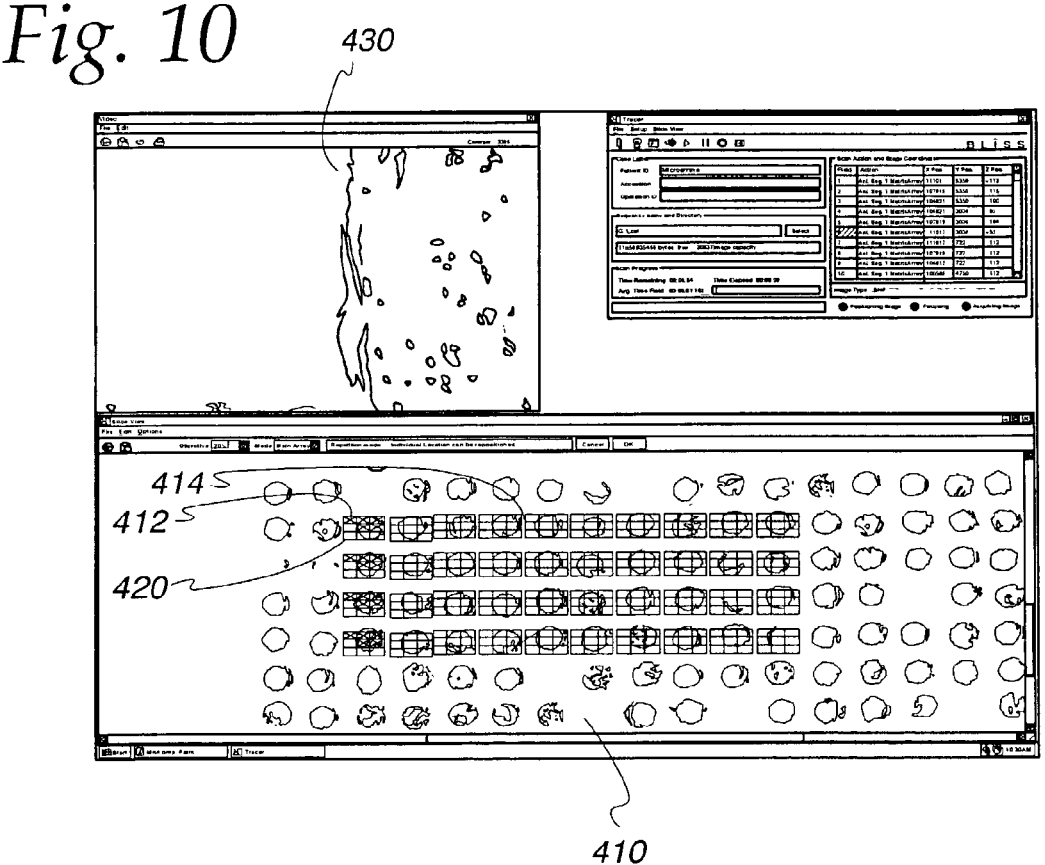
FIG. 10 is a screen shot showing a gridding system having been set up on a tissue dot-by-tissue dot basis, and the beginning of a scan occurring on a 3×3 image tile grid covering an upper, left-hand dot, and a 4×10 array of dots with five of the image tiles having been filled or scanned for the first tissue dot for the apparatus shown in FIG. 1.

The results of such a recentering may best be seen in FIG. 10 wherein a low magnification window 410 having a plurality of dots also has 3×3 tiled grids 412 formed thereover. It may be appreciated that the tile grids are not strictly in registration or in contact with one another as there are open spaces 414 positioned therebetween. However, each of the tiled grids completely covers the individual dot image which is to be tiled or scanned. A scan pattern is set up moving back and forth across the 3×3 rows and columns as may best be seen for the tile grid 412 wherein five of the nine tiles are shown with X's formed therein and indicating that those tiles have already been scanned. The next tile to be scanned is shown in magnified form in a high magnification window 430 shown on the screen.

Figure 11:
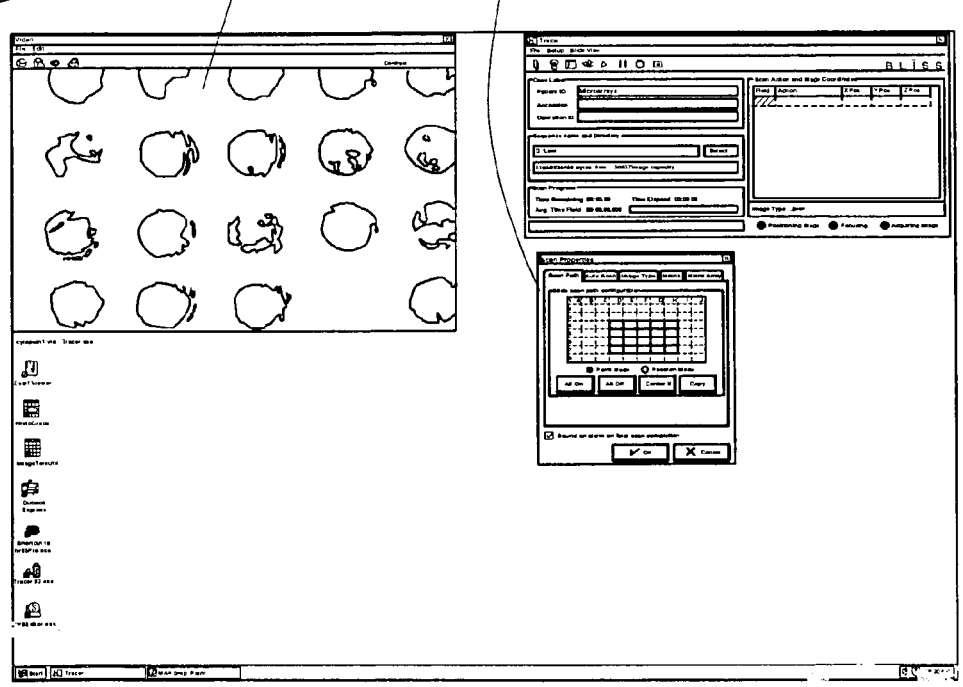
FIG. 11 is a screen shot showing a magnified view of the tiled dot images after having been scanned for the apparatus shown in FIG. 1.
Figure 12:
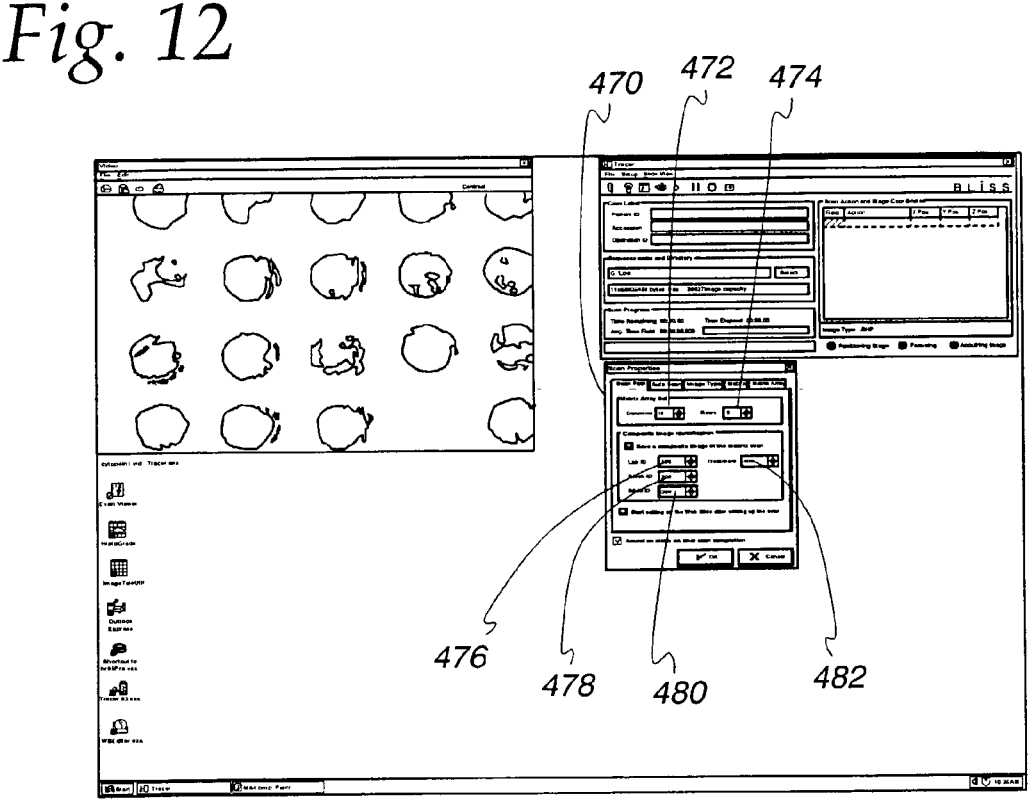
FIG. 12 is a magnified view of the dot images after having been scanned showing the addition of a lab ID, a block ID, and a slide ID for the apparatus shown in FIG. 1.

Subsequent to scanning or before scanning, slide scan paths may be changed or reconfigured as shown by a dialog box 450 shown in FIG. 11 along with a low magnification window 452 of a portion of a microarray.

Also subsequent to scanning the tiled images and assembled into seamless tiled images of the dots for display including panning and scanning. Each of the dots in the matrix array is selected by a dialog box 470 which identifies the dot in the matrix array by column number 472, row number 474, and then assigns a lab ID 476, a block ID 478, a slide ID 480 and a treatment ID 482 to the dot. Patient ID's may also be assigned. These identifications are then associated with the dot image as it is stored on the hard disk drive in both low magnification tiled format and high magnification tiled format image format.

Figure 13:
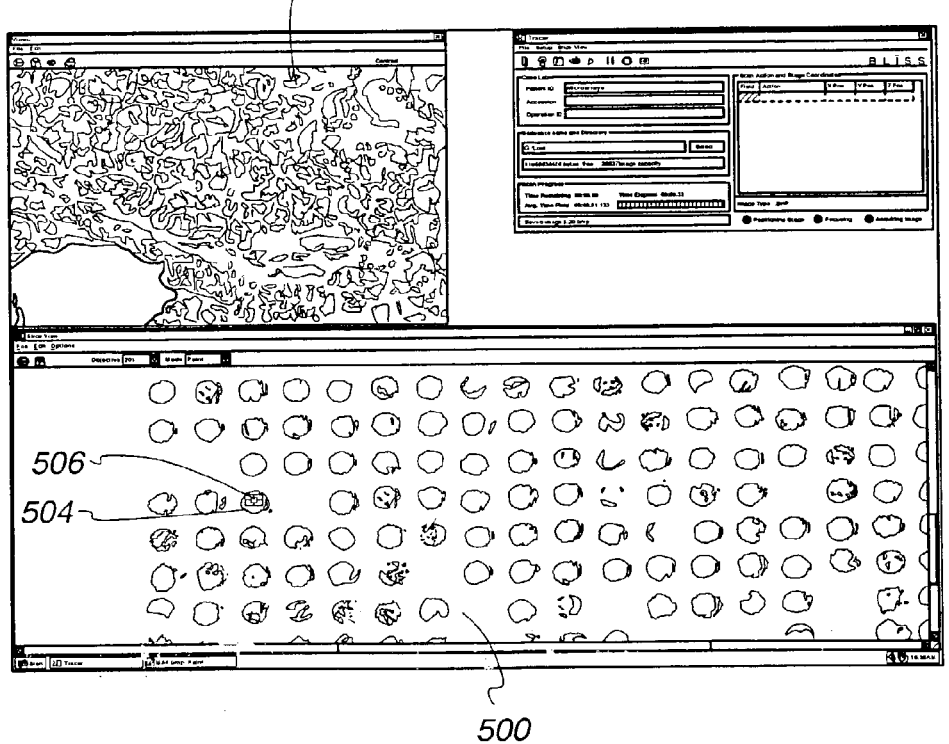
FIG. 13 is a view showing a selected portion identified by a rectangular boundary of one of the dots from the dot image and a magnified view of the bounded region at 20 power for the apparatus shown in FIG. 1.
Figure 14:
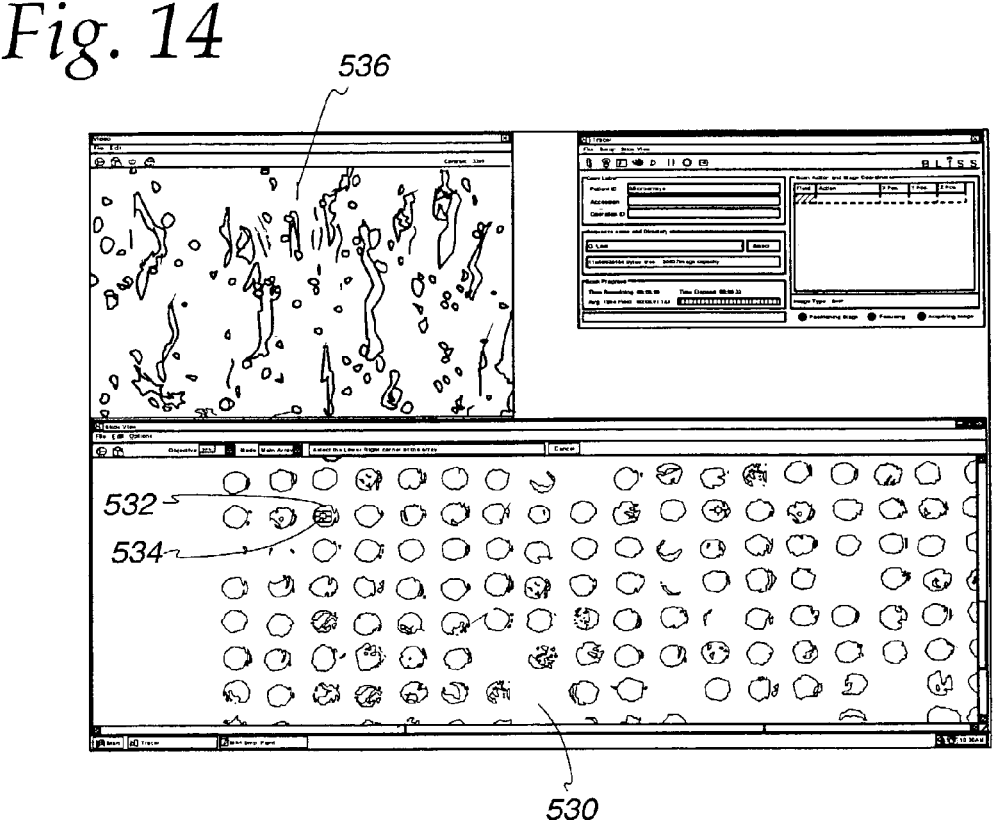
FIG. 14 is a set-up array for a series of dots showing a portion of the tissue from one dot at 20 power magnification for the apparatus shown in FIG. 1.

Low magnification and high magnification display of portions of the microarray may be carried out in a low magnification window 500 and a high magnification simultaneous window 502 as shown in FIG. 13. The high magnification window 502 is selected from a dot 504 by a high magnification window select region or rectangle 506 placed thereover. In this case the high magnification window 502 shows a 20-power magnification of a stained tissue sample such as from a breast cancer or the like. High magnification windows may also be identified as shown in FIG. 14 where in a low magnification window 530 the dot array has a dot 532 with a high magnification identification box or rectangle 534 identified therein. The high magnification or 20-power view of the tissue is shown in window 536.

Figure 15:
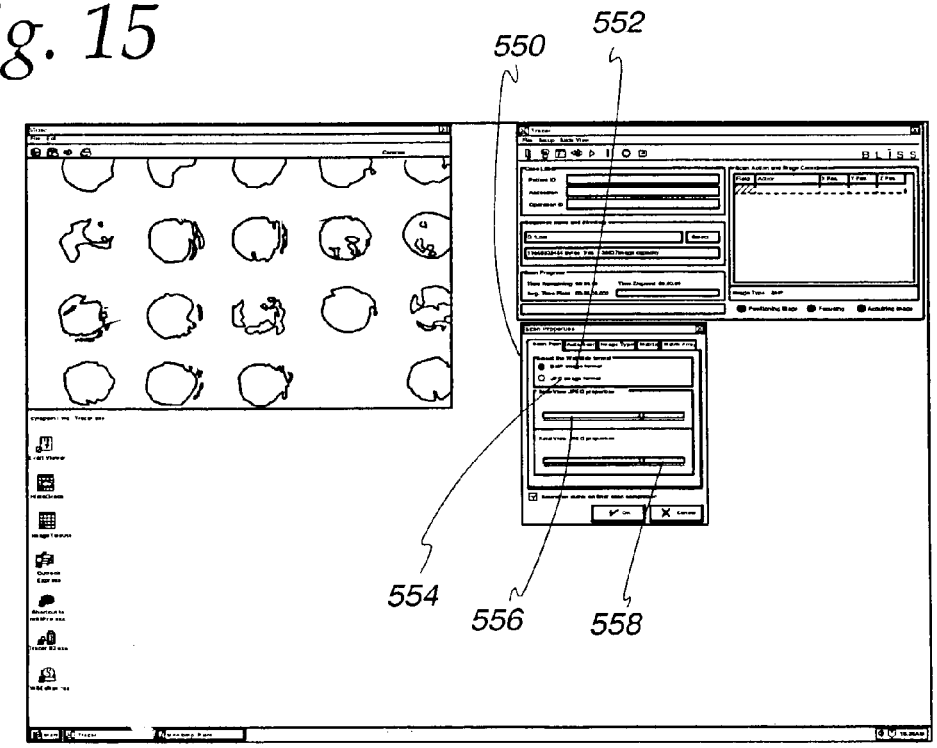
FIG. 15 is a view of a portion of the microarray dots wherein an uncompressed or BMP image format has been selected but also providing the ability to select a compressed or JPEG image format including selection of slide-view JPEG properties and field-view JPEG properties for the apparatus shown in FIG. 1.

The dot images may be stored in compressed or uncompressed format. A dialog box is provided to the user as shown in FIG. 15. The dialog box 550 allows the user to select uncompressed BMP image format 552 or compressed JPEG image format 554. In addition the amount of compression of the slide view 556 and for the field view 558 are user selectable by dialog box slides.

It may be appreciated then that the instant invention provides a convenient and rapid way to analyze and identify hundreds or thousands of microarray tissue samples quickly and conveniently during a molecular assay study.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. A method of analyzing dots having cellular material and arranged in a microarray comprising:
   providing a microscope slide with a microarray of dots thereon arranged in columns and rows;
   acquiring a low magnification image of the microarray showing the magnified dots and their respective positions in the microarray;
   using low magnification image of the dots and their respective locations to locate the dots within the microarray for analysis; and
   performing an analysis for a dot image located from the low magnification image.

2. A method in accordance with claim 1 comprising:
   indexing the low magnification image of the dot and the analysis thereof with a unique identifier associated with the row and column location of the dot within the microarray on the microscope slide.

3. A method of analyzing dots having cellular material and arranged in a microarray comprising:
   providing a microscope slide with a microarray of dots thereon arranged in columns and rows;
   acquiring a low magnification image of the microarray showing the magnified dots and their respective positions in the microarray;
   using low magnification image of the dots and their respective locations to locate the dots within the microarray for analysis;
   performing an analysis for a dot image located from the low magnification image; and
   providing a higher magnification image of the located dot and performing an analysis on the high magnification image of the located dot.

4. A method in accordance with claim 3 comprising:
   performing the analysis by making a quantitative measurement on the located dot.

5. A method in accordance with claim 3 comprising:
   forming a data structure for a dot comprising data for dot specimen identification, column and row location, and the analysis made for the dot.

6. A method in accordance with claim 3 comprising:
   forming a data base with data structures having the dot images associated with a unique specimen identifier so that the dot images can be later identified, accessed and displayed.

7. A method in accordance with claim 3 wherein the low magnification image of the dots comprises:
   acquiring successive, adjacent images of the microarray and assembling them together into a composite image.

8. A method in accordance with claim 7 comprising:
   tiling of successive and adjacent images of single fields of view to form the composite image.

9. A method of analyzing dots having cellular material and arranged in a microarray comprising:
   providing a microscope slide with a microarray of dots thereon arranged in columns and rows;
   acquiring a low magnification image of the microarray showing the magnified dots and their respective positions in the microarray;
   using low magnification image of the dots and their respective locations to locate the dots within the microarray for analysis;
   performing an analysis for a dot image located from the low magnification image; and
   acquiring and tiling adjacent high magnification images of a single field of view for each dot located from the low magnification image of the microarray of dots.

10. A method in accordance with claim 9 comprising:
    performing a quantitative measurement analysis on the tiled high magnification images; and
    indexing the high magnification images and the low magnifications with unique identifiers associated with the row and column position of the associated dot on the microscope slide.

11. A method of analyzing dots having cellular material and arranged in a microarray comprising:
    providing a microscope slide with a microarray of dots thereon arranged in columns and rows;
    acquiring a low magnification image of the microarray showing the magnified dots and their respective positions in the microarray;
    using low magnification image of the dots and their respective locations to locate the dots within the microarray for analysis;
    performing an analysis for a dot image located from the low magnification image;
    providing several microarrays on the same microscope slide with each of the microarrays having hundreds of dots thereon;
    forming a database for the images of the dots; and
    indexing the respective dot images with a unique identifier associated with the location of dots in each of the microarrays on the microscope slide.

12. An apparatus for analyzing specimen dots having cellular material and arranged in a microarray on a microscope slide, the apparatus comprising:
    a microscope for providing magnified images of the dots from the specimen dots on the microscope slide;
    an imager for providing signals representative of a magnified image for each of the specimen dots;
    a display coupled to the imager and operable to display a microarray of magnified dot images in their respective positions within the microarray to assist in locating a specimen dot image for analysis; and
    a processor connected to the display and operable to index an analysis made from the magnified dot image with the specimen dot in the microarray on the microscope.

13. An apparatus in accordance with claim 12 wherein the imager displays adjacent magnified dot images positioned adjacent one another to form a composite magnified image of the dot images, each in positions associated with the specimen dots in the microarray.

14. An apparatus in accordance with claim 12 wherein:
    the microscope and imager are operable by the processor to provide a high magnification image of each specimen dot in the microarray.

15. An apparatus in accordance with claim 14 wherein:
    the processor stores low magnification images and high magnification images and indexes them to their associated specimen dot in the microarray on the microscope slide.

16. A method of capturing images of a microarray of tissue samples on a microscope at low and high magnifications for retrieval and display, the method comprising:
    acquiring a low magnification image of the microarray showing a grid of tissue samples from the slide;

selecting a sub-array of a grid of tissue images displayed at low magnification;

acquiring high magnification images of the located tissue samples within the subarray; and associating unique identification information with each of the respective tissue sample images in the microarray so that individual tissue samples in the microarray can be selected and high magnification images thereof be acquired for evaluation.

17. A method in accordance with claim 16 wherein the associating of unique identification information with each tissue sample comprises:

associating a row and column index for the tissue sample images with row and column positions of the tissue samples in the microarray.

18. A method in accordance with claim 16 comprising:

performing a quantitative analysis from the tissue sample images.

19. A method in accordance with claim 18 wherein the quantitative analysis comprises:

making an evaluation of cellular structure and tissue architecture.

20. A method in accordance with claim 18 wherein the quantitative analysis comprises:

discovery of genes and targeting genetic probes for attachment to particular tissue regions and molecules.

21. A method in accordance with claim 18 wherein the quantitative analysis comprises:

using antibody-based probes.

22. A method in accordance with claim 16 wherein the low magnification image of the microarray comprises:

tiling of adjacent field of view images acquired at low magnification to be used to provide a composite low magnification image of the micro-array.

23. A method in accordance with claim 16 comprising:

displaying a grid scanning pattern related to image tiling at high magnification for each of the respective tissue samples.

24. A method in accordance with claim 16 comprising:

providing high magnification images of the tissue specimen and performing assays thereon.

25. An apparatus for capturing images of a microarray of tissue samples on a microscope slide at low and high magnifications for retrieval and display, the apparatus comprising:

a microscope for providing low and high magnification views from tissue samples on the microscope slide;

an imager for acquiring images of the tissue samples;

a display for displaying acquired images from the imager;

a processor coupled to the imager;

the processor being operable for selecting and displaying a sub-array of a grid of tissue images at low magnification;

the processor being operable with imager and display for acquiring high magnification images of tissue samples in the microarray; and the processor operable for associating index information with the low magnification images so that individual tissue samples in the microarray can be accessed for evaluation.

26. An apparatus in accordance with claim 25 comprising:

the processor being operable for storing the position of each of the tissue sample in the array in both X and Y coordinates and in row and column locations.

27. An apparatus in accordance with claim 25 comprising:

the processor being operable for tiling of adjacent fields of view images of a sample into a composite, high magnification view of a tissue sample.

28. An apparatus in accordance with claim 25 comprising:

the processor being operable for tiling adjacent fields of view images acquired at low magnification into a composite, low magnification view of the microarray.

29. An apparatus in accordance with claim 25 comprising:

the display displaying simultaneously to a viewer a low magnification image of the microarray and a high magnification image of at least a portion of one of the tissue samples.

30. An apparatus in accordance with claim 25 comprising:

a moveable marker displayed to the user and movable by the user to a center location on a circular tissue sample to locate the center of a circular tissue sample.

31. An apparatus in accordance with claim 25 comprising:

the processor operating the display to display center markers at uniformly spaced positions on which the microarray samples should be centered if properly positioned at uniform locations in the grid.

32. An apparatus in accordance with claim 25 comprising:

the processor operating to the display for displaying a grid over each of the tissue samples in the sub-array.

33. An apparatus in accordance with claim 25 comprising:

the display being operable for simultaneously displaying both high and low magnification images.

34. A data structure for a microarray of tissue samples on a microscope slide comprising:

low magnification image data being embodied in a computer-readable storage medium for providing an image at low magnification of the microarray of tissue samples on a microscope slide;

high magnification image data being embodied in a computer-readable storage medium for providing an image at high magnification of a tissue sample for evaluation;

data being embodied in a computer-readable storage medium for connecting the high magnification data for a tissue sample image with the low magnification image of the same tissue sample in the microarray; and index identification data being embodied in a computer-readable storage medium for each of the tissue sample images in the microarray to identify the tissue sample image with the tissue sample in the microarray.

35. A data structure in accordance with claim 34 comprising:

data being embodied in a computer-readable storage medium from a quantitative analysis of the tissue sample image within the microarray.

36. A data structure in accordance with claim 34 wherein the low magnification image data comprises:

image tile data being embodied in a computer-readable storage medium acquired for adjacent fields of view from the microscope usable to form a low magnification composite image of the microarray.

37. A data structure in accordance with claim 34 wherein the high magnification image comprises:

image tile data being embodied in a computer-readable storage medium for adjacent portions of a tissue sample for being stitched together to form a composite high magnification image for each tissue sample.

38. A data structure in accordance with claim 34 wherein the index identification data comprises:

row and column data being embodied in a computer-readable storage medium for each image to associate the image with a tissue sample in the microarray.

39. A data structure in accordance with claim 34 comprising:
  stored data information for use in remote manipulating into view of both the low magnification image of the microarray and a high magnification image from at least a portion of the tissue sample selected for viewing.

40. A data structure in accordance with claim 34 comprising:
  data stored in a computer-readable storage medium to locate each of several microarrays on a microscope slide and to locate within each microarray image the low magnification tissue images at the same precise positions in the grid as occurs in each microarrays on the microscope slide.

41. A data structure in accordance with claim 40 wherein the data stored for the low magnification image of a tissue sample dot in a grid of data on the microarray accurately positions an irregularly spaced tissue sample dot relative to uniform grid spacing where the non-uniform spacing occurs for the tissue dot on the slide.

42. A data structure for a microarray of tissue sample images and identification information for each of the tissue samples in the microarray comprising:
  low magnification, image data being embodied in a computer-readable storage medium for adjacent tiles of sub-arrays of tissue samples;
  information data being embodied in a computer-readable storage medium to align adjacent image tiles into a composite image of the microarray of samples;
  quantitative analysis data being embodied in a computer-readable storage medium for the tissue samples of the microarray; and
  identification data being embodied in a computer-readable storage medium for each of the tissue samples in the microarray to allow retrieval of the quantitative analysis data and retrieval of a specifically identified tissue sample image for display.

43. A data structure for a microarray of tissue sample images and identification information for each of the tissue samples in the microarray comprising:
  low magnification, image data being embodied in a computer-readable storage medium for adjacent tiles of sub-arrays of tissue samples;
  information data being embodied in a computer-readable storage medium to align adjacent image tiles into a composite image of the microarray of samples;
  quantitative analysis data being embodied in a computer-readable storage medium for the tissue samples of the microarray;
  identification data for each of the tissue samples in the microarray to allow retrieval of the quantitative analysis data being embodied in a computer-readable storage medium and retrieval of a specifically identified tissue sample image for display; and
  high magnification image data being embodied in a computer-readable storage medium and comprising image tile data for adjacent fields of view images for each tissue sample.

44. A data structure in accordance with claim 43 comprising:
  information data being embodied in a computer-readable storage medium stored to align adjacent high magnification, image tiles for a tissue sample to allow scrolling of adjacent high magnification images into view.

45. A data structure for a microarray of tissue sample images and identification information for each of the tissue samples in the microarray comprising:
  low magnification, image data being embodied in a computer-readable storage medium for adjacent tiles of sub-arrays of tissue samples;
  information data being embodied in a computer-readable storage medium to align adjacent image tiles into a composite image of the microarray of samples;
  quantitative analysis data being embodied in a computer-readable storage medium for the tissue samples of the microarray;
  identification data being embodied in a computer-readable storage medium for each of the tissue samples in the microarray to allow retrieval of the quantitative analysis data and retrieval of a specifically identified tissue sample image for display;
  high magnification image data being embodied in a computer-readable storage medium for displaying high magnification from the tissue samples; and
  data being embodied in a computer-readable storage medium associating the low magnification image data of a tissue sample with the high magnification image data for displaying a high magnification view from a portion of a tissue sample being displayed at low magnification.

46. A data structure for a microarray of tissue sample images and identification information for each of the tissue samples in the microarray comprising:
  low magnification, image data being embodied in a computer-readable storage medium for adjacent tiles of sub-arrays of tissue samples;
  information data being embodied in a computer-readable storage medium to align adjacent image tiles into a composite image of the microarray of samples;
  quantitative analysis data being embodied in a computer-readable storage medium for the tissue samples of the microarray;
  identification data being embodied in a computer-readable storage medium for each of the tissue samples in the microarray to allow retrieval of the quantitative analysis data and retrieval of a specifically identified tissue sample image for display;
  high magnification image data being embodied in a computer-readable storage medium for displaying high magnification from the tissue samples; and
  stored data information being embodied in a computer-readable storage medium for use in remote manipulation into view of both the high magnification and low magnification images for a tissue sample selected.

47. An apparatus for producing a low magnification image of a microarray of tissue samples and high magnification images of adjacent portions within each tissue sample, comprising:
  a microscope for carrying a microscope slide having a microarray of tissue samples;
  an imager connected to the microscope to acquire magnified images of the microarray and of the tissue samples;
  a display connected to the imager for displaying tissue sample images;

a processor coupled to the imager and operable in a first mode to acquire a low magnification image of the microarray;

the processor being operable in a second mode to cooperate with the imager to acquire high magnification images of tissue samples displayed at low magnification; and the processor being operable in a third mode for indexing a tissue sample image with a tissue sample in the microarray.

48. An apparatus in accordance with claim 47 comprising:

a remote display device to receive over a common communication channel the aforesaid data to display thereon a composite image of the microarray and a composite image of several fields of view of tissue sample at high magnification.

49. An apparatus in accordance with claim 47 wherein:

the processor is operable in a fourth mode to provide a scanning pattern to locate tissue samples irregularly spaced in grid of the microarray.

50. An apparatus in accordance with claim 49 comprising:

a marker positionable with respect to the irregularly spaced tissue dot to cause the imager to acquire high magnification images as determined by the marker's position.

51. A method of analyzing tissue dots arranged in columns and rows in a microarray on a microscope slide, the method comprising:

scanning the microarray of tissue dots and providing magnified images of the microarray with the tissue dots in their respective columns and rows within the microarray;

identifying each of the tissue dot images with respect to its row and column position of the tissue dot within the microarray;

performing an analysis of a respective magnified image of a tissue dot;

associate each analysis with each identified tissue dot to allow a later review of a tissue dot image and its analysis from the microarray.

52. A method in accordance with claim 51 comprising:

performing a quantitative analysis on the tissue dot.

53. A method in accordance with claim 51 comprising:

providing a composite magnified image of the tissue dots; and using the composite magnified image to locate tissue dots for analysis at higher magnification.

* * * * *